(12) United States Patent
Andersson et al.

(10) Patent No.: US 9,035,661 B2
(45) Date of Patent: May 19, 2015

(54) CONDUCTIVITY SENSOR ASSEMBLY

(75) Inventors: Lars Andersson, Uppsala (SE); Stefan D'Argy, Uppsala (SE); Patric Fricking, Uppsala (SE); Joachim Tollstoy, Linkoping (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 180 days.

(21) Appl. No.: 13/518,501

(22) PCT Filed: Dec. 20, 2010

(86) PCT No.: PCT/SE2010/051427
§ 371 (c)(1),
(2), (4) Date: Jun. 22, 2012

(87) PCT Pub. No.: WO2011/078774
PCT Pub. Date: Jun. 30, 2011

(65) Prior Publication Data
US 2012/0256641 A1   Oct. 11, 2012

(30) Foreign Application Priority Data
Dec. 22, 2009   (SE) ...................................... 0951014

(51) Int. Cl.
*G01R 27/28*   (2006.01)
*G01R 27/22*   (2006.01)
*G01N 27/07*   (2006.01)
*G01N 27/08*   (2006.01)
*G01N 30/64*   (2006.01)

(52) U.S. Cl.
CPC ............... *G01R 27/22* (2013.01); *G01N 27/07* (2013.01); *G01N 27/08* (2013.01); *G01N 2030/645* (2013.01)

(58) Field of Classification Search
USPC ........ 324/649, 438, 439, 450, 695, 71.4, 639, 324/693; 73/61.44, 152.28, 861; 702/7, 13, 702/45, 50, 49, 100
See application file for complete search history.

(56) References Cited

U.S. PATENT DOCUMENTS

| 3,424,975 | A |   | 1/1969  | Sanford et al. |
| 5,441,049 | A |   | 8/1995  | Masano |
| 5,945,830 | A | * | 8/1999  | Magowan et al. ............. 324/438 |
| 7,481,118 | B2 | * | 1/2009 | Nyfors ............................ 73/861 |
| 7,562,587 | B2 | * | 7/2009 | Atkinson et al. ........... 73/861.63 |
| 2007/0255527 | A1 | * | 11/2007 | Schick et al. .................. 702/179 |
| 2009/0201035 | A1 | * | 8/2009  | Kaltenbach et al. .......... 324/695 |

FOREIGN PATENT DOCUMENTS

| EP | 0397274   | * 11/1990 | ............. G01N 33/04 |
| EP | 0 397 274 |   2/1994  |  |
| JP | 56-151975 |   11/1981 |  |
| JP | 59084148  |   5/1984  |  |
| JP | 402102445 |   4/1990  |  |
| JP | 08-102445 |   4/1996  |  |
| JP | 408220036 |   8/1996  |  |

(Continued)

*Primary Examiner* — Arleen M Vazquez
*Assistant Examiner* — Neel Shah (57) ABSTRACT

A flow-through conductivity sensor assembly comprises a housing (4) having a flow passage with an inlet end and an outlet end. The cross section of at least a section of the flow passage extension between the inlet and outlet ends is divided into a conductivity measuring channel (2) and a parallel bypass channel (3) of larger cross-sectional area than the measuring channel (2).

13 Claims, 7 Drawing Sheets

(56) References Cited

FOREIGN PATENT DOCUMENTS

| | | | |
|---|---|---|---|
| JP | 10132775 | 5/1998 | |
| JP | 2005-241590 | 9/2005 | |
| JP | 2005241590 | * 9/2005 | ............ G01N 27/06 |
| JP | 2008-058024 | 3/2008 | |
| WO | WO 2005/095935 | 10/2005 | |

* cited by examiner

CONDUCTIVITY SENSOR ASSEMBLY

CROSS-REFERENCE TO RELATED APPLICATIONS

This application is a filing under 35 U.S.C. 371 of international application number PCT/SE2010/051427, filed Dec. 20, 2010, published on Jun. 30, 2011 as WO 2011/078774, which claims priority to application Ser. No. 0951014-0 filed in Sweden on Dec. 22, 2009.

FIELD OF THE INVENTION

The present invention relates to measurement of conductivity, and more particularly to a sensor assembly for measuring the conductivity of a flowing liquid.

BACKGROUND OF THE INVENTION

Conductivity, or electrolytic conductivity, is defined as the ability of a substance to conduct electrical current. Conductivity is the reciprocal of resistivity, and its basic unit is siemens per meter (S/m). For a liquid, the conductivity is a summation of contributions from all ions present in the liquid.

The measurement of the conductivity of liquids is usually performed in a so-called conductivity cell. Conductivity cells can be classified according to the technique by which they interact with the sample and also by the geometry of the cell design. The two operating techniques used are the contacting technique, and the inductive or toroidal technique. In both cases, an AC electrical input signal is applied to the conductivity cell, and the resultant AC electrical output signal from the cell is measured (a DC electrical signal would cause changes in the electrolyte).

Cells that measure conductivity using the contacting technique have their electrodes in direct contact with the liquid to be tested, whereas cells using the toroidal technique include two toroidal coils that are not in contact with the liquid.

The alternating current frequency typically ranges between 50 Hz and 50 kHz, depending on the electrolyte concentration of the liquid, the measurement frequency being increased with increasing ion concentration in the liquid in order to avoid interfering capacitance effects due to polarization effects at the electrodes.

A basic conductivity cell of the contact type has two parallel electrode plates, e.g. made from platinum. When an AC voltage is applied across the plates, an AC current will flow through the liquid which is inversely proportional to the electrical resistance between the electrodes, and thereby proportional to the conductivity of the liquid in the cell.

The resistance, R, of the cell is proportional to the distance, d, between the electrodes and the cross-sectional area, A, of the electrodes. The ratio d/A is usually referred to as the "cell constant" $\Theta$, i.e. $\Theta = d/A$.

For measurement on liquid flows, the conductivity cell is usually of flow-through type and coupled in-line with a liquid flow conduit. In this type of conductivity cell, the electrodes typically include two or more annular electrodes spaced along the stream of flow of the liquid. In this case, the cell constant will be defined by the ratio of the distance between the electrodes and the cross-sectional area of the conduit section between the electrodes.

The cell constant indicates the approximate range of conductivities that the cell can measure. In general, cells with a low cell constant should be used for measuring low conductivities, whereas a high cell constant is required for higher conductivity measurements.

U.S. Pat. No. 3,424,975 discloses a conductivity cell for measuring the electrical conductivity of flowing liquids in which the length of the electrical path, and therefore the resistance, of a conductivity cell can be varied to suit any particular use of the cell. In one embodiment, two parallel flow paths for the liquid are provided. One flow path is through three conduits in series which are formed of electrically conductive material. Conduits of electrically insulating material extend from the central conductive conduit into the outer conductive conduits to provide elongated electrical paths between the central conductive conduit and the outer conductive conduits. A valve is provided in the second flow path to permit relative adjustment of flows through the two paths.

U.S. Pat. No. 5,441,049 discloses a conductivity cell having a passageway through which liquid flows with a constriction in the passageway for regulating the flow and providing a predetermined cross-sectional area for measuring conductivity. Electrodes, which are preferably cylindrical, having their longitudinal axes parallel with the passageway, are located on each side of the constriction. For such a conductivity cell having a given length and outside diameter, a cell constant in the range from one to one hundred can be obtained by varying cell parameters including inside diameter at the constriction, inside diameter at the ends, inside diameter at the electrodes, and center-to-center spacing of the electrodes.

In many process flow systems, e.g. cross-flow filtration systems, a low hold-up volume is highly desired. However, when scaling up a conductivity cell type designed for laboratory applications which has a certain cell factor, to the piping diameters used in process flows, keeping the same cell factor will considerably increase the length of the conductivity cell and result in undesired large hold-up volumes. Conductivity cells of the prior art types mentioned above do not provide any solution to this problem.

It is therefore an object of the present invention to provide a conductivity cell for large diameter piping applications, such as bio-process flows, which overcomes the above-mentioned problem of increased cell length and hold-up volumes.

Summary of The Invention

According to the present invention, there is provided a new conductivity sensor cell design which can be used in association with piping diameters of process system sizes while keeping the same cell factor as for a smaller version conductivity cell, or even increasing it, without adding hold-up volume to the system.

This conductivity cell, or conductivity sensor assembly, which is defined in claim 1, is based on the concept of passing a portion of the liquid flow through a parallel flow channel where the conductivity measurement takes place. Thereby the cross-sectional area as well as the length of the cell are reduced, which thus reduces the hold-up volume of the flow or piping system in which the conductivity cell is mounted.

In a preferred embodiment, a pH flow-cell is integrated into the conductivity sensor assembly which will further reduce the hold-up volume of the liquid flow system.

Additional preferred embodiments are set forth in the dependent claims.

In the following, the invention will be described in more detail, by way of example only, with regard to a non-limiting embodiment thereof, reference being made to the accompanying drawings.

DETAILED DESCRIPTION OF THE INVENTION

As mentioned above, the present invention is related to a flow-through type conductivity sensor, below frequently referred to as conductivity cell, for measuring the electrical conductivity of a liquid flow. The liquid flow is particularly a process flow, such as a chromatography column process flow or a cross-flow filtration process flow, where piping of relatively large dimensions are used and minimizing hold-up volumes is of importance.

The conductivity cell of the invention is of the type where conductivity is measured by applying an AC current between spaced electrodes in contact with the liquid. The electrodes are preferably circular, or annular, surrounding the liquid path. In such a cell, the "cell factor" (which is constant for a given cell) is the "distance between electrodes" divided by the "cross sectional area of the current", i.e. the cross sectional area of the liquid flow.

Assume that a certain conductivity cell of this type has a length of 10 cm and an inside diameter of 1 cm. If such a cell is dimensioned to be coupled in-line in a process flow piping system by increasing the inside diameter to, say, 5 cm, it would be necessary to increase the length to 2.5 m to keep the same cell factor. It is readily seen that this would introduce a substantially increased hold-up volume, which in many process applications, such as in cross-flow filtration systems, would be highly undesired.

According to the present invention, it is possible to keep the same cell factor, or even increase it, by introducing a small parallel flow where the conductivity measurement takes place in order to thereby reduce the critical cross-sectional area and thus also reduce the length of the cell. In this way no hold-up volume is added to the flow system in which the conductivity cell is mounted in-line.

An embodiment of a conductivity sensor cell according to the present invention will now be described with reference to FIGS. 1 to 4.

In the following, terms such as "upper" and "lower", "top" and "bottom", etc are used merely with reference to the geometry of the embodiment of the invention shown in the Figures and are not intended to limit the invention in any manner.

Figure 1:
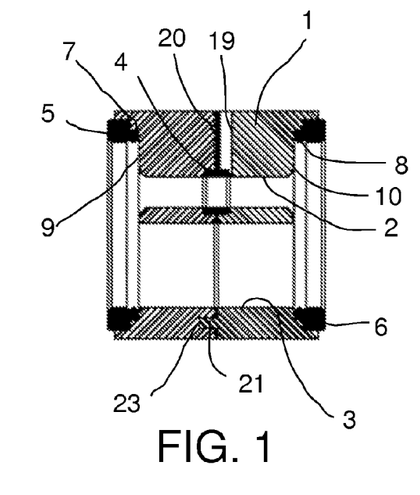
FIG. 1 is a cross-sectional view of an embodiment of a conductivity cell according to the present invention.
Figure 2:
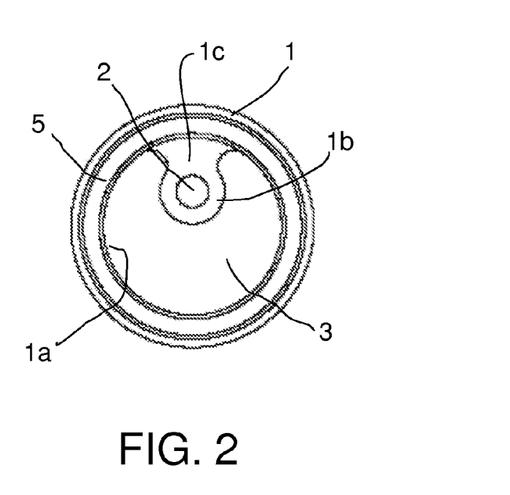
FIG. 2 is an end plan view of the conductivity cell embodiment in FIG. 1.

The illustrated conductivity cell comprises a cylindrical body 1, the interior of which is divided into two parallel passageways or channels of different cross-sectional areas, viz. a small area channel 2, and a large area channel 3 which occupies the rest of the interior cross section of the body 1. This embodiment of conductivity cell may be said to comprise a first tubular member 1a having a second tubular member 1b with smaller diameter attached to its inner wall via a connecting portion 1c (FIG. 2).

The small area channel 2 is to function as measuring channel and has a first circular, or annular, electrode 4, intended to serve as a signal or measuring electrode, located in the middle of the channel 2 and having the same inner diameter as the channel 2. Second and third annular electrodes 5 and 6, respectively, intended to function as ground electrodes, are mounted via o-rings 7, 8 in respective stepped recesses 9, 10 at each end of the cylindrical body 1.

Figure 3:
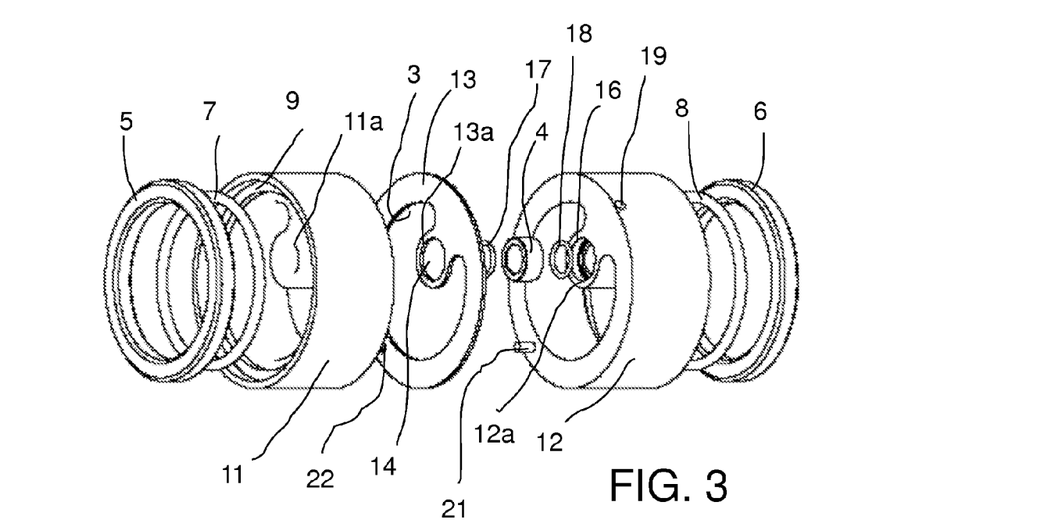
FIG. 3 is an exploded isometric perspective view of the conductivity cell embodiment in FIGS. 1 and 2.

With specific reference to FIG. 3, the body 1 is here assembled from three separate major parts, viz. two end parts 11 and 12, and a central part 13 which is clamped between them and supports the centre of annular electrode 4 in a circular aperture or bore 14 in the portion 13a thereof forming part of the measuring channel 2.

The ends of annular electrode 4 are received in corresponding recesses 15, 16, via o-rings 17, 18, in the portions 11a and 12a, respectively, of body parts 11, 12 that form the measuring channel 2. As is seen in FIG. 1, a radial bore 19 in the body part 12 receives a conductor wire or rod connected to the signal electrode 4.

A guiding pin 21 on the body part 12 is received in corresponding bores 22 and 23 in the body parts 13 and 11, respectively.

The body parts 11-13, or at least the portions thereof forming the flow channels 2 and 3, are made of an electrically insulating material, preferably plastic. Depending on the intended use, the material may be required to sustain high temperatures, e.g. steam of 130° C. In such a case, the material may be selected from polyalkenes (polyolefins), such as polyethylene or polypropylene, which also have low water absorbance.

The electrodes 4-6 are typically of metal (e.g. titan or platinum), but may also be made from conducting plastic or carbon.

The cell factor of the conductivity cell formed by the measuring channel 2 together with electrodes 4 and 5, 6 is defined by the diameter (or rather the cross-sectional area) of the measuring channel 2 and the axial distance between the signal electrode 4 and each ground electrode 5, 6.

The cross-sectional area of the measuring channel 2 is preferably substantially smaller than that of the wider by-pass channel 3. While the ratio of the cross-sectional area ratio of the measuring channel to the that of the by-pass channel may vary within relatively wide limits, it is typically less than about 1:2, and preferably less than about 1:4, e.g. in the range of about 1:5 to about 1:30.

Although the conductivity cell is particularly suitable for use in connection with process flow pipe diameters of the size used in e.g. cross-flow filtration, it may be adapted for use with smaller flow pipe diameters, in practice, however, preferably not smaller than about 10 mm.

In FIGS. 1 to 4, the circular ground electrodes 5, 6 are provided outside of the measuring channel 2 and have a diameter corresponding to that of the wider flow channel 3. Alternatively, the ground electrodes may have the same diameter as the signal electrode 4 and be placed within the measuring channel (preferably at or close to the ends thereof).

Although, basically, a single ground electrode 5 or 6 could be sufficient (one electrode at or near each end of the measuring channel), the provision of two ground electrodes, one on each side of the measuring electrode, ensures that ground potential is not obtained from some part of the piping system which would lead to erroneous measurement values. With dual ground electrodes it is also not critical in which direction the conductivity cell is positioned in the piping system.

In the conductivity cell embodiment described above, the measuring channel 2 is disposed adjacent to the inner periphery of the large area channel 3. For simplicity, as mentioned above, this may be seen as a large diameter tube or conduit having a small diameter tube or conduit attached to its inner wall. The measuring channel, i.e. the small diameter conduit, could, however, be placed at any position in the cross-section of the large diameter conduit, e.g. centrally therein.

While the conductivity cell embodiment described above, as well as embodiments to be described hereinafter, have two flow paths or channels, it is also possible to have three or even more channels, with one of the channels being a measuring channel (i.e. provided with a signal electrode), and the other channels serving as by-pass channels.

In another such multiple flow channel embodiment, channels of different diameters or cross-sectional areas may be provided, each having a signal electrode. With such a conductivity cell the cell factor may be varied by selection of the channel to function as measuring cell by coupling its signal electrode to the monitor circuit used.

Provided that a certain pressure change is acceptable, the flow passage diameter of the conductivity cell may optionally be at least slightly smaller than the piping system to which is mounted.

The liquid flow in the conductivity cell may be laminar or turbulent.

To measure the conductivity, an AC voltage is applied across the electrodes and the current (I) through the liquid is measured to determine the conductivity (I/V). In the present case, an AC voltage is applied across the signal electrode 4 and the ground electrodes 5, 6 which will cause a current to flow from electrode 4 in parallel paths to electrodes 5 and 6. By placing a suitable meter in the circuit (not shown) the conductivity of the liquid flowing through the measuring channel (and the large diameter channel 3) can be determined. Typically, however, the conductivity cell is connected via cable to a transmitter which converts the received signals to a measurement value or send them to a computer system.

When measuring conductivity, in order to minimize the influence of capacitance effects (so called "double layer" capacitance caused by polarization at the electrodes) it is common practice to increase the frequency of the applied AC voltage with increasing ion concentration of the liquid to be measured. To this end, instruments are available which automatically, in dependence of the salt concentration, switch between a number (usually three or four) different fixed measurement frequencies.

An improvement in this measuring technique which enables automatic selection of optimal frequencies for each possible situation (such as varying electrolyte concentration, temperature changes etc), and in association with which the conductivity cell of the present invention is advantageously used, is disclosed in U.S. Pat. No. 5,504,430 (the entire disclosure of which is incorporated by reference herein). In this approach, an AC voltage is applied over the conductivity cell, and in response to a conductance value calculated from the output of the cell, an expected frequency of the AC voltage is generated. The AC voltage is then set to the calculated value. The above steps are repeated until two conductance determinations differ only by a predetermined absolute value. This value is then displayed and registered as the true conductance of the tested liquid.

Figure 4:
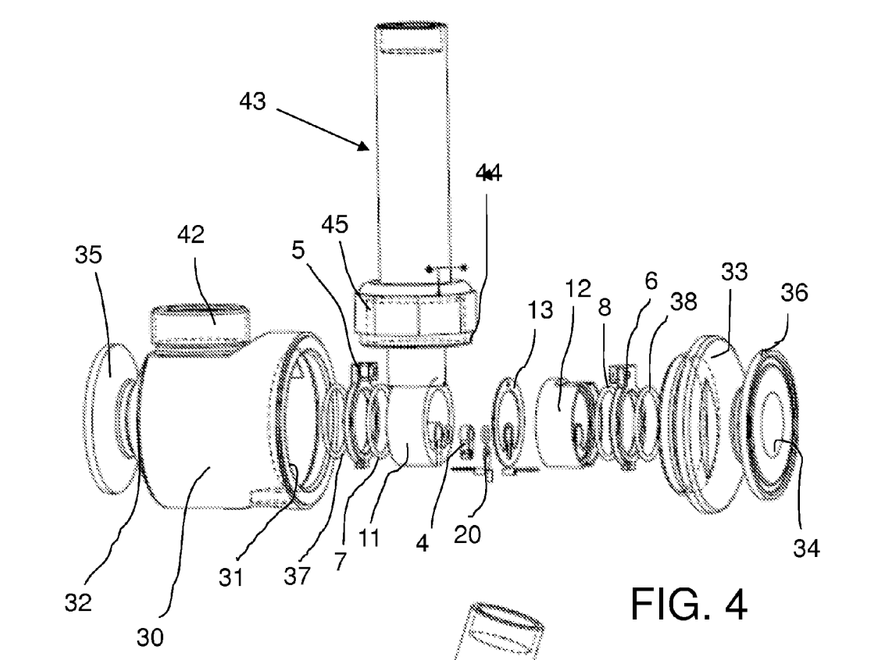
FIG. 4 is an exploded (partially transparent) isometric perspective view of a combined conductivity and pH sensor assembly to be mounted in a process flow system and including the conductivity cell embodiment shown in FIGS. 1 to 3.
Figure 5:
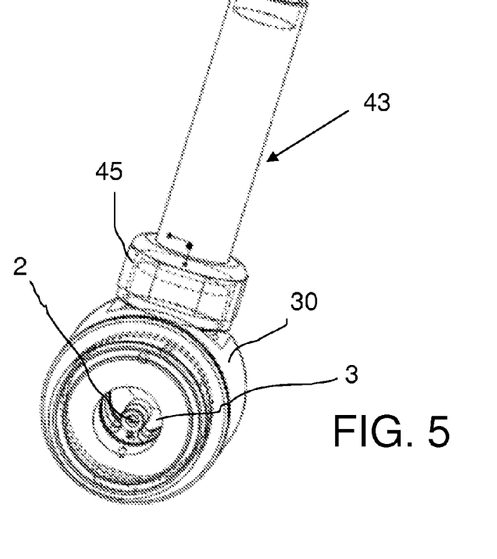
FIG. 5 is an isometric view of the assembly in FIG. 4 in the assembled state.
Figure 6:
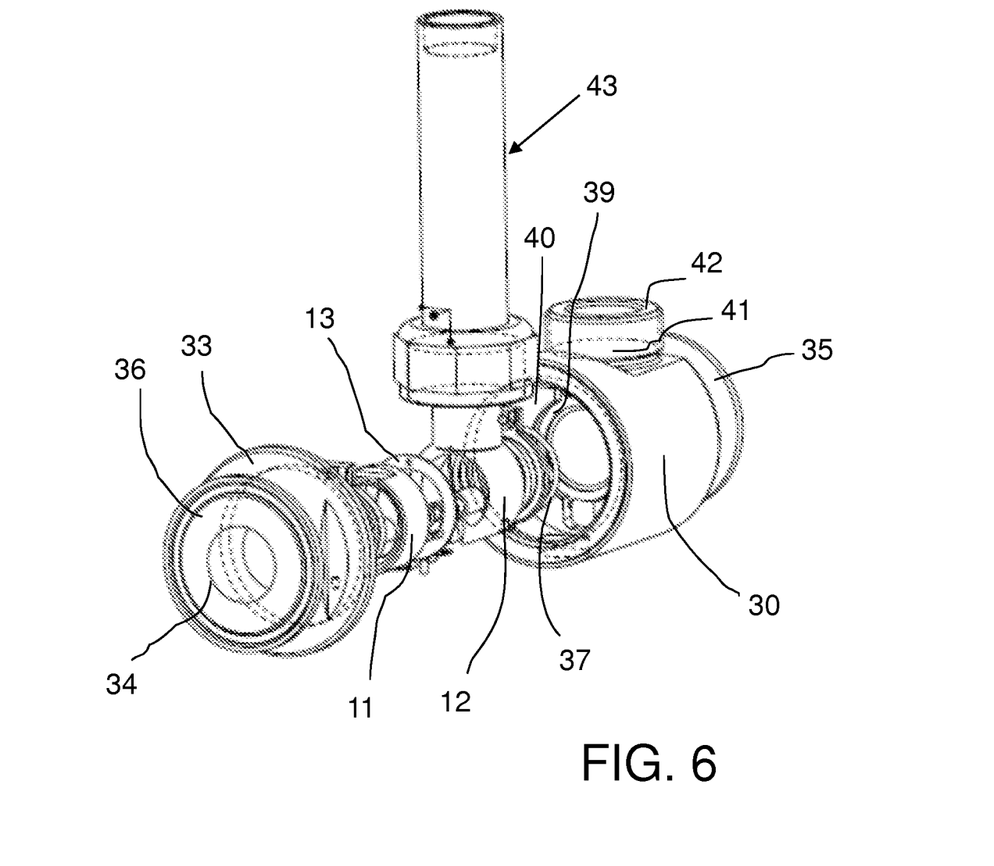
FIG. 6 is another exploded (partially transparent) isometric view of the assembly in FIGS. 4 and 5.

In FIGS. 4 to 6, wherein the same reference numerals as in FIGS. 1 to 3 are used for identical parts, there is shown a conductivity cell assembly in which a pH flow cell is integrated. This assembly comprises a housing 30 having an internal cavity 31 adapted to accommodate the conductivity cell shown in FIGS. 1 to 3.

At each end, the cavity 31 is partially closed by slightly frusto-conically shaped end pieces 32 and 33, respectively, each having a circular opening 34 (FIG. 6) at least substantially corresponding to the diameter of the large area channel 3 of the conductivity cell. The end pieces are attached to the housing 30, e.g. via bolts or screws received in bores (not shown) in the end pieces and threaded bores (not shown) in the end edges of the housing 30. Each end piece 32, 33 has an integral flange portion 35 and 36, respectively, for coupling the conductivity cell to a piping system, e.g. a process flow system (not shown).

The conductivity cell, shown in FIGS. 1-3 and described above, is received within the housing cavity 31, connecting at each end, via a ground electrode 5, 6 and an o-ring 37, 38, to a circular opening 39 in a transverse partition wall 40 (FIG. 6) of the housing spaced from the end piece 32.

The space between the end piece 32 and the partition wall 40 also communicates with a transverse bore 41 in the housing 30 opening in a threaded connecting piece 42. A pH meter or probe 43 having a stop flange 44 is received in the bore 41 and secured in place by a nut element 45 and an o-ring (not shown).

Integrating a pH flow cell with the conductivity cell in an assembly as described above will, of course, further reduce the total hold-up volume.

Another embodiment of combined conductivity and pH sensor assembly is illustrated in FIGS. 7 to 14, where the conductivity cell and the pH cell are defined in a single body or housing 50, which e.g. may be manufactured by injection moulding.

Figure 7:
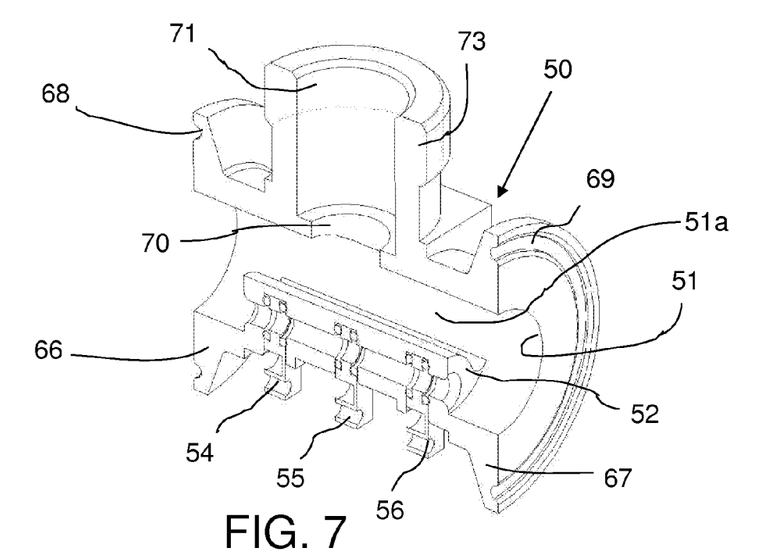
FIG. 7 is a midline cutaway isometric perspective view of another embodiment of a conductivity cell provided with means for receiving a pH sensor.
Figure 8:
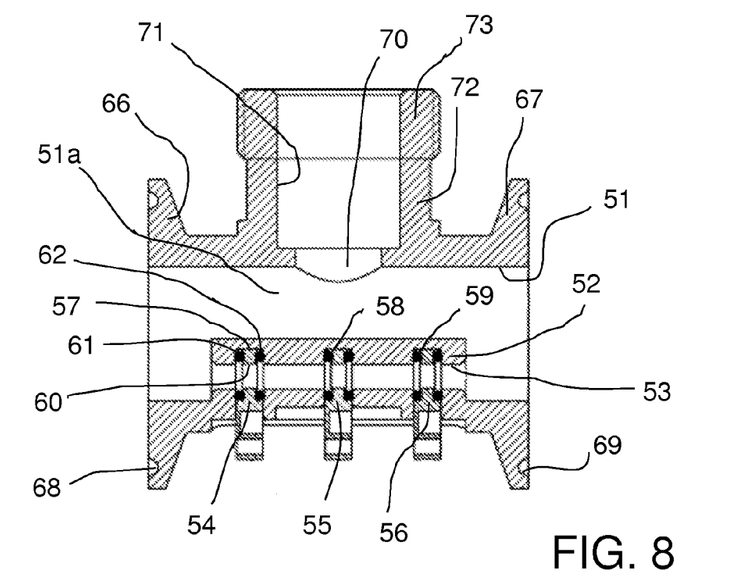
FIG. 8 is a cross-sectional view corresponding to the perspective view in FIG. 7.

The housing 50 has a flow-through channel 51 of generally circular cross-section. Along a major portion of channel 51 there is an inward protrusion 52 with a bore 53 which defines a parallel flow channel of substantially smaller diameter than that of the channel 51, the remaining part of the channel 51 forming a by-pass channel 51a. The flow channel 53 has mounted therein three (here identical) electrode elements 54 to 56 (e.g. of titan) which are received in respective recesses 57 to 59 in the housing.

Figure 14:
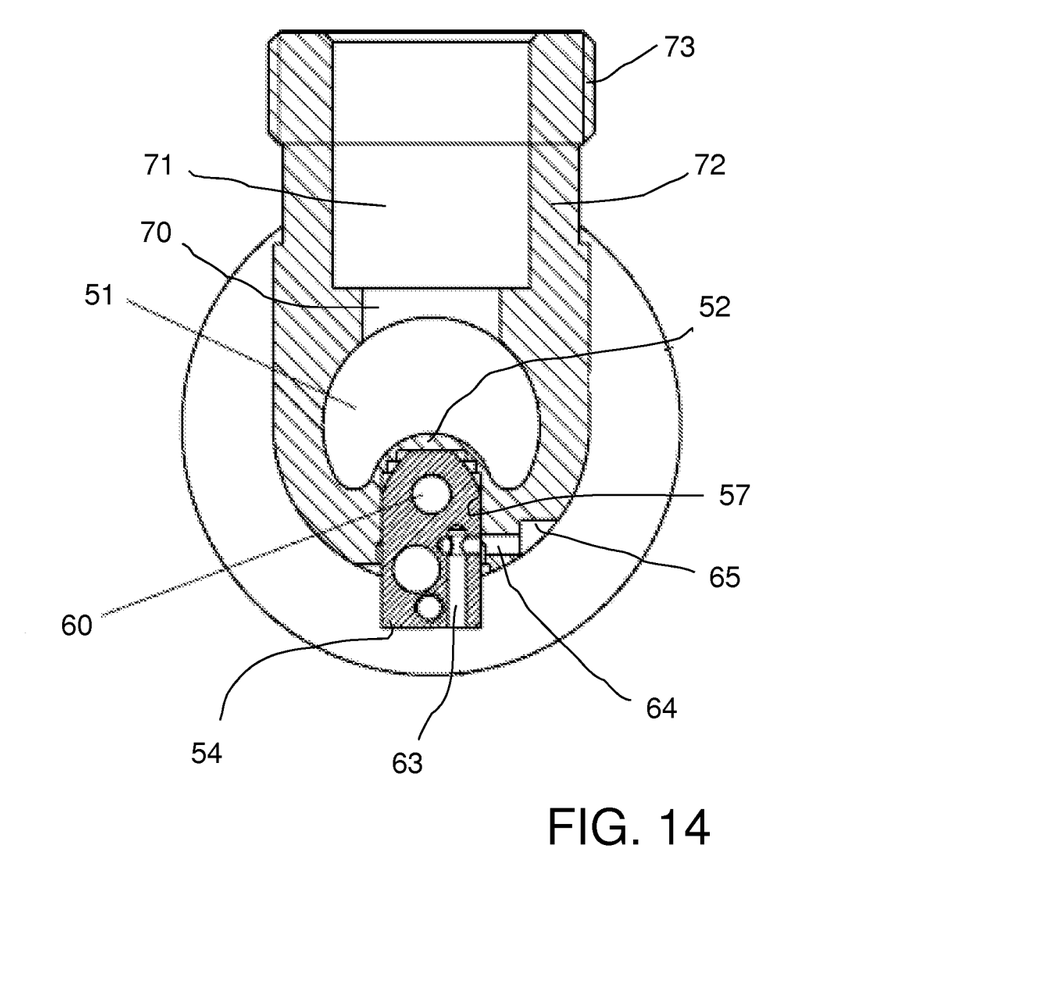
FIG. 14 is a cross-sectional view of the conductivity cell shown in FIGS. 7 and 8 through an electrode thereof.

With reference now to FIG. 14, each electrode element 54-56 has a through-hole, indicated at 60 for electrode element 54, of the same diameter as the flow channel 53, thereby forming an annular electrode within the channel 53. Sealing against the walls of each recess 57-59 is effected by respective pairs of o-rings, in FIGS. 8 and 9 designated by reference numerals 61 and 62 for the electrode element 54. As in the conductivity cell embodiment described above, the central electrode element 55 provides the signal or measuring electrode, and the electrode elements 54 and 56 on either side thereof provide the ground electrodes. Together, the flow channel 53 and the electrode elements 54-56 form a "conductivity cell".

In the illustrated case, with reference to FIG. 14 again, each electrode element 54-56 has a (in the figure) vertical recess 63 for receiving an electric connecting wire or cable (not shown). A (in the figure) horizontal threaded bore 64 for a stop screw (not shown) extends transversely from an external recess 65 in the housing 50, crossing the recess 63. The stop screw secures the electrode element 54 in the recess 57 in place, while simultaneously clamping the electrical connecting cable in the vertical recess 63.

At each end the housing 50 has flange members 66 and 67 for mounting of the sensor assembly to a piping system where conductivity and pH are to be measured. Each flange 66, 67 has a groove 68 and 69, respectively, for receiving an o-ring/gasket (not shown).

Transversely to the flow channel 51, and opposite to the flow channel 53, a bore 70 is provided in the housing which connects channel 51 with a bore 67 of a transverse tubular extension of the housing 50 forming a connecting piece 72 for a pH sensor or probe, the top part 73 of which is threaded.

Figure 9:
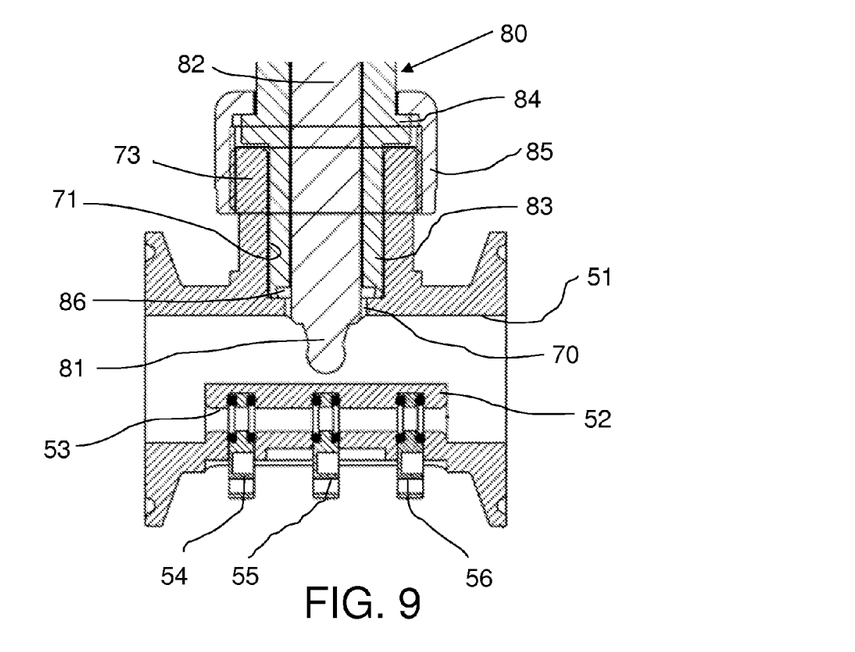
FIG. 9 is corresponding view to that in FIG. 8 but with a partially shown pH sensor assembled thereto.
Figure 10:
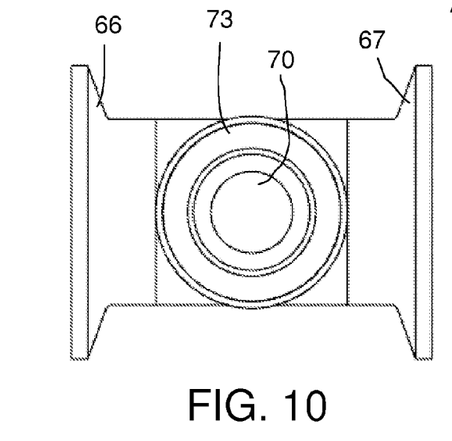
FIG. 10 is a top plan view of the conductivity cell shown in FIG. 8.
Figure 11:
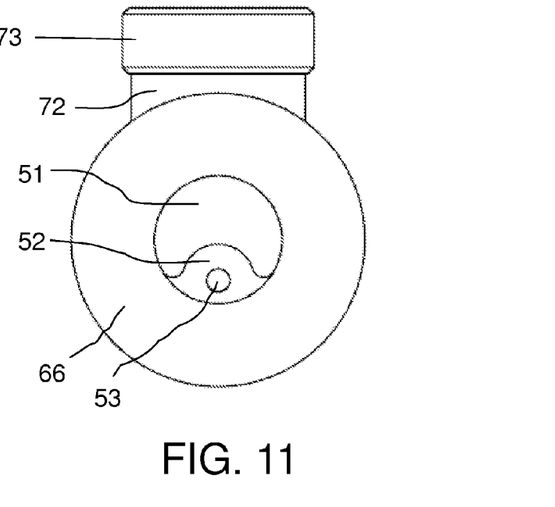
FIG. 11 is an end plan view of the conductivity cell shown in FIG. 8.
Figure 12:
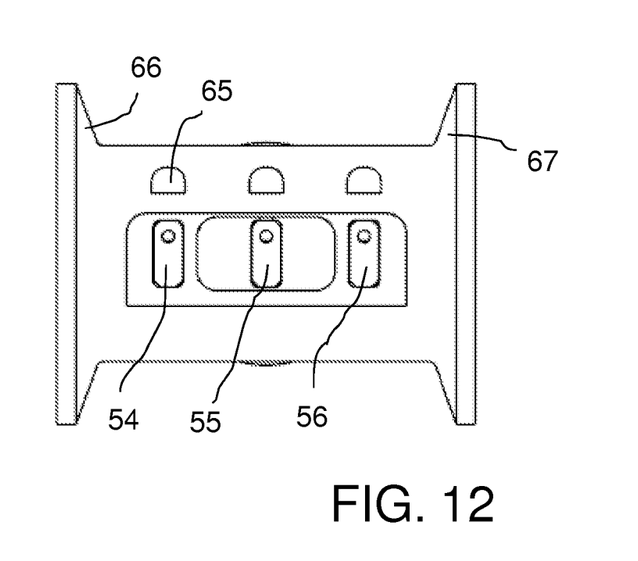
FIG. 12 is a bottom plan view of the conductivity cell shown in FIG. 8.
Figure 13:
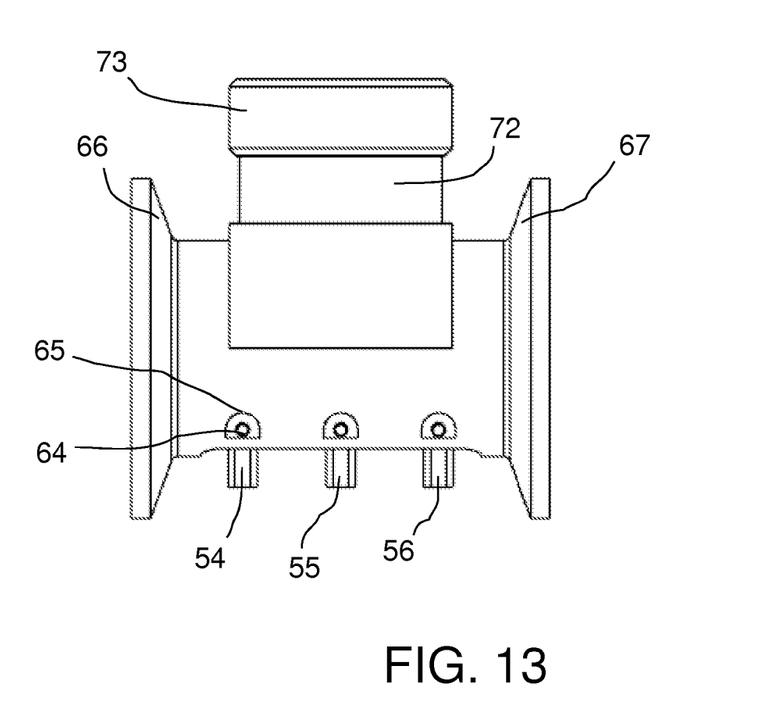
FIG. 13 is another side plan view of the conductivity cell shown in FIG. 8.

In FIG. 9, a pH sensor meter, or probe, 80 is inserted into the bore 71 of the connecting piece 72, such that the probe end 81 extends into the flow channel 51 for contacting a liquid flowing therein. The illustrated probe 80 has a generally cylindrical core portion 82 within a tubular casing 83 having an outer diameter corresponding to that of the bore 71 in the connecting piece 72.

The core end 81 of the probe 80 passes through the bore 70 in the wall of channel 51, whereas the bottom end of the casing 83 abuts the bottom of bore 71. A flange portion 84 is provided on the casing 83 to substantially abut the top surface of the connecting piece 72 when the pH probe 80 is fully inserted. A nut member 85 engaged with the threading of the connecting piece 72 locks the probe in place. Sealing of the probe end 81 against the bore 71 is ensured by an o-ring (not shown) in a groove 86 at the bottom end of the probe casing 83.

In the embodiment illustrated in FIGS. 7-14 and described above, the ratio of the cross-sectional area of the measuring channel 53 to the cross-sectional area of the bypass channel part 51a is about 1:22, the ratio of the cross-sectional area of the measuring channel to the total cross-sectional area of the channel 51 being about 1:30. It is understood, however, that these ratios may vary within wide limits to suit any particular application. Typically, the ratios will be smaller, the greater the diameter is of the piping system into which the conductivity cell is mounted. For example, while for a measuring channel diameter of 4 mm and a connected pipe diameter of 25 mm, the cross-sectional area of the measuring channel to the cross-sectional area of the pipe is 1:39, an increase of the connected pipe diameter to 50 mm would give a ratio of 1:156. Larger pipe sizes would give even lower ratios."

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A flow-through conductivity sensor assembly for bio-process flows, comprising a housing (1; 50) having a flow passage (51) with an inlet end and an outlet end, wherein the cross section of at least a section of the flow passage extension between the inlet and outlet ends is divided into a conductivity measuring channel (2; 53) and a parallel by-pass channel (3; 51a) of larger cross-sectional area than the measuring channel, wherein the conductivity measuring channel (2; 53) is placed in the cross-section of the by-pass channel (3; 51a), wherein a first and a second electrode are provided adjacent to a respective end of the measuring channel and wherein a first electrode (4; 55) is provided within the measuring channel (2; 53) and a second electrode (5, 6; 54, 56) is provided adjacent to one or each end of the measuring channel (2; 53).

2. The conductivity sensor assembly of claim 1, wherein the cross-section of the measuring channel (2; 53) is at least substantially circular.

3. The conductivity sensor assembly of claim 1, wherein the measuring channel is disposed adjacent to the inner periphery of the flow passage.

4. The conductivity sensor assembly of claim 1, wherein the second electrode (54, 56) is disposed within the measuring channel (53).

5. The conductivity sensor assembly of claim 1, comprising annular electrodes (5, 6; 54-56).

6. The conductivity sensor assembly of claim 5, wherein the electrodes are made of metal.

7. The conductivity sensor assembly of claim 5, wherein the electrodes surround a liquid path through the measuring channel.

8. The conductivity sensor assembly of claim 1, wherein the ratio of the cross-sectional area of the measuring channel (2; 53) to the cross-sectional area of the by-pass channel (3; 51a) is less than about 1:2, preferably less than about 1:4, more preferably less than about 1:10, for especially less than about 1:30.

9. The conductivity sensor assembly of claim 1, wherein the by-pass flow channel is divided into at least two separate flow paths.

10. The conductivity sensor assembly of claim 1, further comprising a pH probe (43; 80) exposed to fluid flowing in the flow passage (51).

11. The conductivity sensor assembly of claim 10, wherein the pH probe (80) extends into the by-pass channel (51a).

12. The conductivity sensor assembly of claim 10, wherein the housing (50) is a single-piece unit.

13. The conductivity sensor assembly of claim 12, wherein at least the measuring electrode is provided by an electrode element (55) mounted in a recess (58) extending through the housing (50) transversely to the measuring channel (53).

* * * * *